United States Patent
Goedecke et al.

(10) Patent No.: US 6,221,294 B1
(45) Date of Patent: Apr. 24, 2001

(54) PROCESS FOR THE PRODUCTION OF CYANURIC CHLORIDE MOLDINGS

(75) Inventors: Ralf Goedecke; Klaus Hentschel, both of Rodenbach; Rolf-Dieter Möller, Babenhausen; Knut Ehrhardt, Hanau; Manfred Schmidt, Geinhausen; Michael Kissner, Seligenstadt, all of (DE)

(73) Assignee: Degussa Aktiengesellschaft, Frankfurt (DE)

( * ) Notice: Subject to any disclaimer, the term of this patent is extended or adjusted under 35 U.S.C. 154(b) by 0 days.

(21) Appl. No.: 09/593,946

(22) Filed: Jun. 15, 2000

Related U.S. Application Data

(62) Division of application No. 08/950,794, filed on Oct. 15, 1997, now abandoned.

(30) Foreign Application Priority Data

Oct. 15, 1996 (DE) .............................................. 196 42 449

(51) Int. Cl.[7] ........................................................ B29D 7/00
(52) U.S. Cl. .................... 264/141; 264/144; 264/157; 264/212; 264/330; 264/299; 264/316
(58) Field of Search ................................ 264/5, 138, 140, 264/141, 144, 157, 212, 330, 299, 316; 544/190, 218, 219

(56) References Cited

U.S. PATENT DOCUMENTS

| 3,427,314 | 2/1969 | Sims . | |
|---|---|---|---|
| 3,709,648 | * 1/1973 | Kuhnlein | 264/212 |
| 3,925,377 | 12/1975 | Geiger . | |
| 3,941,784 | 3/1976 | Nelson . | |
| 4,244,722 | * 1/1981 | Tsuya et al. | 264/212 |
| 4,250,308 | 2/1981 | Goedecke . | |
| 4,271,298 | 6/1981 | Hentschel . | |
| 4,363,769 | * 12/1982 | Tsuya et al. | 264/212 |
| 4,389,357 | * 6/1983 | Chu et al. | 264/212 |
| 4,535,160 | 8/1985 | Elischer . | |
| 4,591,493 | 5/1986 | Klima . | |

FOREIGN PATENT DOCUMENTS

| 2024800 | 3/1991 | (CA) . |
|---|---|---|
| 1 266 308 | 8/1965 | (DE) . |
| 23 32 636 | 1/1975 | (DE) . |
| 28 43 379 | 4/1980 | (DE) . |
| 0 416 584 | 3/1991 | (EP) . |
| 2239872 | 1/1991 | (GB) . |

OTHER PUBLICATIONS

Henglein, E., Lexikon Chemische Technik, 1. Aufl. Seite 233 f, VCH, Weinheim, 1988 (Parat), pp. 233–234.

Kirk–Othmer, Size Enlargement, "Encyclopedia of Chemical Technology", 3d Ed., vol. 21, pp. 77–105, ©1978.

* cited by examiner

Primary Examiner—Jan H. Silbaugh
Assistant Examiner—Kenneth Jones
(74) Attorney, Agent, or Firm—Pillsbury Winthrop LLP

(57) ABSTRACT

Cyanuric chloride moldings, especially tablets and flakes, have advantages over powders in ease of handling. The moldings are produced by droplet or strip application of molten cyanuric chloride on to a surface and dissipation of the latent heat of fusion by cooling the surface or contacting the melt applied as droplets or strips with a cooling gas.

6 Claims, 1 Drawing Sheet

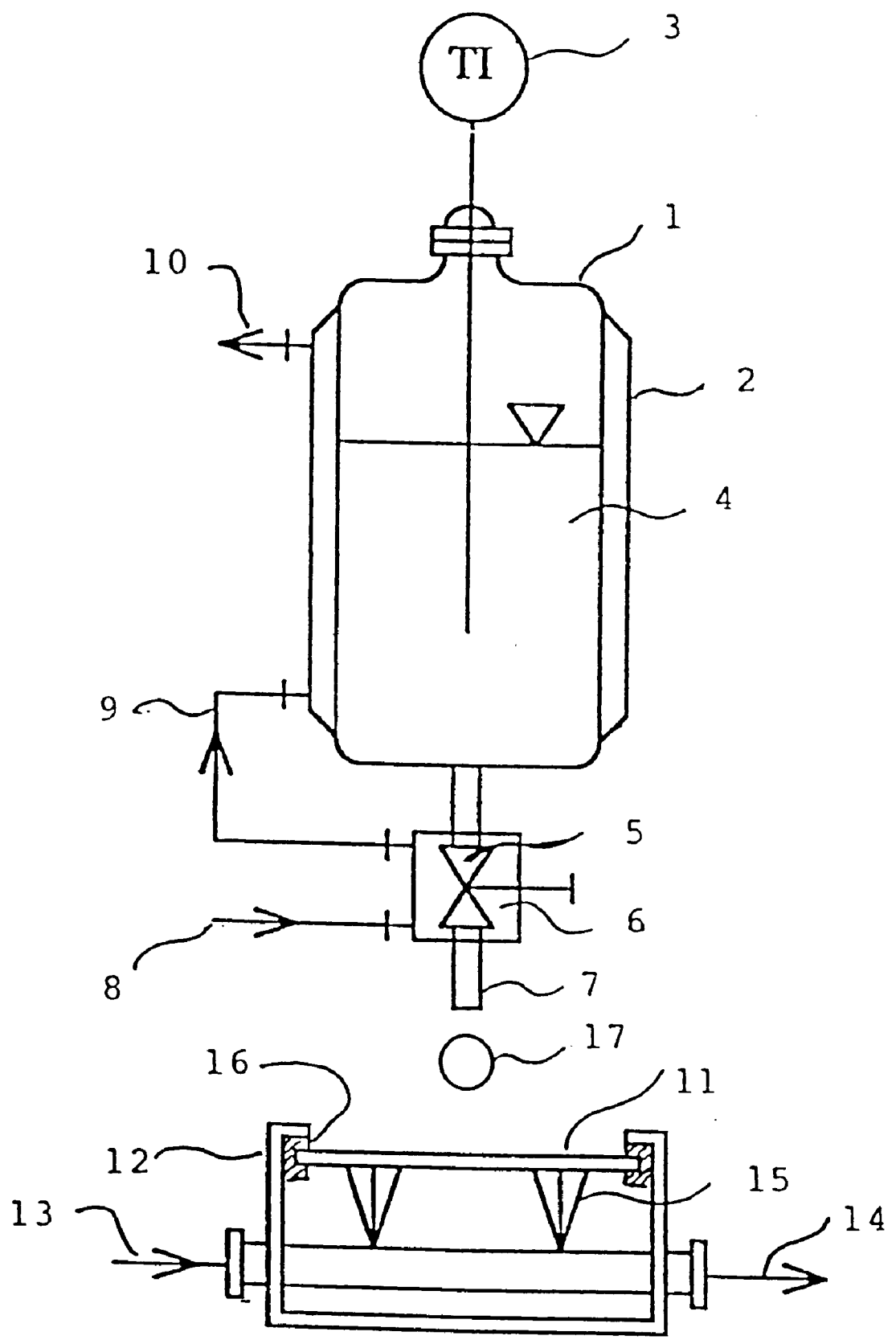

PROCESS FOR THE PRODUCTION OF CYANURIC CHLORIDE MOLDINGS

This is a division of application Ser. No. 08/950,794, filed Oct. 15, 1997, now abandoned.

CROSS-REFERENCE TO RELATED APPLICATION

This application is based on German Application DE 196 42 449.6, filed Oct. 15, 1996, which disclosure is incorporated herein by reference.

FIELD OF THE INVENTION

The present invention relates to a new product form of solid cyanuric chloride, namely moldings, especially those in tablet or flake form, and a process for producing cyanuric chloride moldings, especially tablets and flakes.

BACKGROUND OF THE INVENTION

It is known to convert cyanuric chloride obtained in the form of vapor by trimerization of cyanogen chloride directly or via liquid cyanuric chloride into solid cyanuric chloride in finely particulate form:

The deposition of pulverulent cyanuric chloride by desublimation of cyanuric chloride in vapor form can be carried out in externally cooled chambers or by introducing cyanuric chloride vapor together with an inert gas and/or an inert cooling liquid vaporizing during the deposition process, into a deposition chamber—see for example DE-PS 12 66 308 and U.S. Pat. No. 4,591,493. In the preparation of finely particulate cyanuric chloride from liquid cyanuric chloride the latter is injected through a nozzle into a deposition chamber and cooled with cycled inert cooling gases or by indirect cooling in the deposition chamber until the spray droplets deposit in crystalline form—see for example DE 28 43 379. A common feature of these processes is a considerable technical expenditure on deposition chambers and devices for recycling and purifying the process gases and waste gases.

In the previously evaluated processes as well as processes based on the same principles, cyanuric chloride is always obtained in finely particulate form, in general having a maximum grain diameter of substantially less than 250 $\mu$m. Such finely particulate products are of course advantageous as regards their high reactivity, but have a number of disadvantages that make a different product form desirable for many purposes.

The handling, including conveyance, storage and metering, of finely particulate cyanuric chloride presents special problems since finely particulate substances usually lead to the formation of dusts that have corrosive and irritant properties and require suction purification equipment. In addition cyanuric chloride is sensitive to hydrolysis, and the resultant hydrolysis products can contaminate not only the cyanuric chloride itself but also following product produced therefrom. Finely particulate cyanuric chloride is particularly susceptible to hydrolysis on account of its large surface area. As a result solid deposits are also readily formed in the dust removal equipment and dust-conveying lines. Technically complicated and costly measures and/or equipment are necessary in order to avoid and eliminate resultant malfunctions.

A further disadvantage of finely particulate cyanuric chloride is the unsatisfactory flowability. Although the latter can admittedly be improved by adding flow auxiliaries, for example silicic acids, nevertheless the flow auxiliary reduces the product purity of the cyanuric chloride and possibly also of products prepared therefrom. According to EP-A 0 416 584 the flowability of solid cyanuric chloride prepared by desublimation or spray crystallization can also be improved without adding a flow auxiliary by a shear treatment of the cyanuric chloride in a kneader or mixer, especially at 60 to 120° C.; the finely pulverulent nature of the cyanuric chloride is not however affected by this process, for the mean grain size of typical embodiments is in the range from about 10 to 40 $\mu$m.

As well as the finely particulate form, cyanuric chloride is also commercially available in liquid form. The preparation of cyanuric chloride in liquid form is known for example from DE-PS 23 32 636. The liquid cyanuric chloride product form requires however storage and transporting vessels and containers that can be heated above the melting point of cyanuric chloride. Although such equipment is economical for users having a large and regular demand for cyanuric chloride, this is not the case however for users having a small and/or irregular demand for cyanuric chloride.

SUMMARY OF THE INVENTION

The object of the present invention is accordingly to provide a new solid product form for cyanuric chloride that exhibits the disadvantages of finely particulate cyanuric chloride at least to a considerably lesser extent. In particular the new product form should be easier to handle in order to reduce operational malfunctions and/or health and work safety problems.

This object is achieved by providing cyanuric chloride moldings, especially tablets and flakes. Such moldings conveniently have a thickness in the range from 0.5 to 3 mm, though thicker or thinner moldings are not excluded. Flakes are preferably between about 0.5 and 2 mm thick and tablets between 1 and 3 mm thick. The diameter of ellipsoidal tablets is preferably in the range from 2 to 10 mm, especially 3 to 6 mm. Flakes include flat moldings having the aforementioned thickness, roughly strip-shaped flakes having a width of between 5 and 10 mm and a length of between 10 and 50 mm, or irregularly broken flakes of similar size. Preferred moldings are substantially free of pulverulent cyanuric chloride. The term "substantially free" is understood to mean that a small amount of dust, preferably less than 5 wt. %, especially less than 2 wt. %, formed by abrasion of the moldings and/or by cyanuric chloride that has sublimated on the surface of the moldings, is not excluded.

The product form according to the invention can be bagged and removed from drums and containers without any problem, in other words substantially without dust formation. In the conveyance within a production plant there are no longer any deposits and blockages of pipelines that can be eliminated only with a great deal of effort. On account of the smaller surface compared to finely particulate cyanuric chloride, the danger of caking and hydrolysis is substantially reduced. The moldings according to the invention are also characterized by a higher purity compared to pulverulent cyanuric chloride since the hydrolyzate content is lower and flow auxiliaries are unnecessary. Although the disadvantages of finely particulate cyanuric chloride have been known for a long time and a considerable technical effort and expenditure was necessary in order reliably to be able to process the product despite the disadvantages, it was surprising that the moldings according to the invention, especially tablets and flakes, were not considered before now as a suitable product form for cyanuric chloride. A process for producing cyanuric chloride moldings according to the invention, especially tablets and flakes, comprises the droplet or strip-like application of cyanuric chloride in molten form on to a surface, dissipation of the latent heat of melting of the cyanuric chloride by cooling the surface and/or contacting the melt applied to the surface with a cooling gas, and removing the solidified moldings from the surface.

The surface on which the cyanuric chloride melt is applied may be formed in any suitable way. It may comprise a smooth or structured surface, preferably a smooth surface cooled from the rear side. The surface may also be flat or in the form of a corrugated surface. In the case of a stationary arrangement of a flat cooled surface, additional equipment is required in order to remove the moldings from the surface, for example blade-like removal devices. Equipment known per se is used to cool the rear side of the surface, especially spraying the rear side of the surface with a liquid or gaseous medium or causing such a medium to flow thereover. Instead of removing the latent heat of fusion through the surface, it is also possible to remove this by means of a cooling gas inert with respect to cyanuric chloride, for example cooled air or nitrogen, with which the melt applied to the surface is contacted. In the last mentioned embodiment a cooling gas may for example be fed directly on to the surface, or the surface is transported through a cooled chamber; the surface may for example be a conveyor belt.

According to a preferred embodiment of the process a continuous cooling belt, normally made of a metallic material that is resistant to the corrosive effects of cyanuric chloride, is used as the cooled surface. The cooling belt may be cooled by spraying or causing a cooling medium to flow over the rear side. Preferred cooling media are water and glycols or cooling gases. An indirect cooling, for example by passing the cooling belt over a cooled surface, for example internally cooled rollers or sliding table, is also possible. Equipment with a cooling belt is known and is commercially available. The process can be continuously operated with such equipment.

The cyanuric chloride melt is applied preferably at a temperature in the range from 150 to 190° C. using suitable application devices in droplet or strip-like form or in the form of a broad band on to the surface, for example a cooling roller or cooling belt or a belt conveyed through a cooling chamber, where the droplets solidify in the form of tablets and the strips solidify as flat moldings. Continuous strips can easily be broken up, flakes of irregular shape thereby being obtained.

The diameter of the outlet openings of the application equipment for the melt determines the size of the droplets or the width of the jet and thus the size of the tablets or the width of the strips. In order to produce tablets or strip-like moldings, outlet bores having a diameter of between 1 and 3 mm or outlet slits having a similar width and a width corresponding roughly to that of the desired strip width are preferably used. By breaking up the solidified strips, flakes can be obtained having a height of for example 0.5 to 5 mm, especially 0.5 to 2 mm, and an area of about 10 to 500 mm$^2$, especially 50 to 200 mm$^2$.

The surface tension of cyanuric chloride permits the formation of a stable droplet. On account of the low viscosity of liquid cyanuric chloride the droplets flatten out until they have completely solidified, resulting in ellipsoidal tablets. Application devices operated by hydrostatic pressure, for example nozzles having a diameter of between about 1 and 3 mm, are suitable for applying droplets. A selective metering of the cyanuric chloride melt is also possible using metering pumps and nozzles having a diameter of between 0.5 and 2 mm. With larger nozzle diameters the area-specific heat that has to be dissipated is also larger on account of the larger droplet size. The longer solidification time due to this factor leads to a longer flow period of the cyanuric chloride, resulting in flatter tablets. Since in the case of strip casting no interstices are formed on the cooling belt, flow occurs only at the edge of the strip; subsequently applied cyanuric chloride accumulates on the lower cyanuric chloride layers, resulting in thicker layers. Tablets as well as strips solidify within a few seconds—circa. 15 sec. for cooling from 145° to 35° C.—and can satisfactorily be removed from the cooled surface, for example a cooling belt, without forming clumps or agglomerations. The cyanuric chloride tablets or strip-shaped flakes crystallize completely during the solidification.

BRIEF DESCRIPTION OF THE DRAWINGS

The FIGURE illustrates, diagrammatically, a device for producing tablets and strip-like flakes.

DETAILED DESCRIPTION OF THE PREFERRED EMBODIMENTS

A shown in the FIGURE, the cyanuric chloride melt (4) is contained in the vessel (1) provided with a heating jacket (2) and temperature measuring device (3). The melt passes from the vessel through a metering valve (5) provided with a heating jacket (6) to the nozzle (7). A heat-transfer medium is fed through line (8); the heat-transfer medium passes from the heatable metering valve through the line (9) to the heatable vessel, from where it is removed through line (10). The cooling belt device, in transverse section relative to the transporting direction of the belt, includes the cooling belt (11), a housing (12) for receiving the cooling medium, as well as a feed line (13) and discharge line (14) for this medium. Suitable sealing elements (16) are arranged between the housing and cooling belt in order to prevent any contact between cyanuric chloride vapor and vapors of the cooling medium, for example water vapor. The drive device for the cooling belt and its return are not shown in FIG. 1. The droplets (17) leaving the nozzle fall on to the cooling belt, where they solidify. The length and speed of the cooling belt are such as to permit a complete solidification of the applied melt. In the illustrated embodiment the cooling medium is sprayed on the rear side of the cooling belt.

According to a preferred embodiment, the application surface for the melt is arranged in an enclosed space connected to a waste gas treatment unit, the surface of the enclosed space opposite the application surface being heated to a temperature above the desublimation temperature of cyanuric chloride and/or in which an inert gas stream, for example nitrogen, is passed over the application surface in order to entrain sublimate with the gas.

The process is simple to carry out. The equipment required to carry out the process requires less investment than is needed for conventional deposition chambers plus the requisite additional equipment for spraying a cyanuric chloride melt or for the desublimation of cyanuric chloride vapor. The reduced yield hitherto caused by dust and operational malfunctions in the previously known processes for producing finely particulate cyanuric chloride does not arise in the process according to the invention.

The cyanuric chloride moldings obtainable according to the invention are characterized by the absence of hitherto unavoidable health and work safety problems and by the fact that the tendency to agglomeration and the danger of contamination by hydrolyzate formation is reduced.

The cyanuric chloride moldings according to the invention can be used in the same way as finely particulate cyanuric chloride to produce secondary products from cyanuric chloride. The preparation of the secondary products can be carried out in organic or aqueous phase or in two-phase solvent systems. With conversions in the suspended state it may be convenient to comminute the moldings within the reaction medium, for example by means of a wet-grinding mill.

EXAMPLE

Cyanuric chloride tablets and strip-shaped flakes were produced in the plant shown in the diagram. The cooling belt used was cooled with water (15° C.). The belt speed was 3 m/min. The temperature of the cyanuric chloride melt was 182° to 183° C. By using a nozzle having a diameter of 3 mm, it was possible to achieve a continuous droplet formation with a slight overheating of the melt. Tablets are obtained having an only slightly varying diameter of about 4 mm (±0.2 mm) and a height of about 1.5 mm. The following Table shows some substance data on the tablets according to the invention compared to a conventional finely particulate cyanuric chloride (Quality F from Degussa AG).

TABLE

|  | Tablets | Cyanuric chloride Quality F |
|---|---|---|
| Hydrolyzate content | 0.21% | 0.32% |
| SiO$_2$ content | 0% | 0.14% |

The determination of the hydrolyzate content is based on the fact that hydrolysis products of cyanuric chloride are not soluble in toluene and, after dissolving the cyanuric chloride in toluene, can easily be separated and gravimetrically determined.

What is claimed is:

1. A process for producing cyanuric chloride moldings, formed as tablets or flakes, comprising:

applying a melt of cyanuric chloride in droplet or strip form on to a surface;

removing latent heat of fusion of the cyanuric chloride by cooling the surface and/or by contacting the melt applied to the surface with a cooling gas, thereby solidifying the melt to form solidified moldings; and removing the solidified moldings from the surface.

2. A process according to claim 1, comprising carrying out the process continuously, wherein the surface comprises a cooling belt made of a metallic material, the latent heat of fusion of the melt being dissipated by a cooling medium brought into contact with a rear side of the cooling belt.

3. Process according to claim 1, comprising applying a cyanuric chloride melt having a temperature in a range from 150° to 190° C., in droplet or strip form on to a cooled surface using droplet-forming or strip-forming device having a diameter in a range from 1 to 3 mm.

4. A process according to claim 2, wherein the cooling medium comprises cooling water.

5. A process according to claim 3, wherein the temperature is in a range from 170° to 190° C.

6. A process according to claim 1, wherein the tablets or flakes have a thickness of 0.5 to 3 mm.

* * * * *